(12) United States Patent
Pouget et al.

(10) Patent No.: US 11,229,356 B2
(45) Date of Patent: Jan. 25, 2022

(54) BIOMARKER OF THE COLOUR PERCEPTION OF A MAMMAL SUBJECT BASED ON PUPIL FREQUENCY TAGGING

(71) Applicants: INSTITUT DU CERVEAU ET DE LA MOELLE EPINIERE (ICM), Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); ASSISTANCE PUBLIQUE-HOPITAUX DE PARIS (AP-HP), Paris (FR); SORBONNE UNIVERSITE, Paris (FR)

(72) Inventors: Pierre Pouget, Paris (FR); Pierre Daye, Braine-L'Alleud (BE); Jean Lorenceau, Paris (FR)

(73) Assignees: INSTITUT DU CERVEAU ET DE LA MOELLE EPINIERE (ICM), Paris (FR); CENTRE NATIONAL DE LA RACHERCHE SCIENTIFIQUE (CNRS), Paris (FR); INSTITUT NATIONAL DE LA SANTE ET DE LA RECHERCHE MEDICALE (INSERM), Paris (FR); ASSISTANCE PUBLIQUE-HOPITAUX DE PARIS (AP-HP), Paris (FR); SORBONNE UNIVERSITE, Paris (FR)

(*) Notice: Subject to any disclaimer, the term of this patent is extended or adjusted under 35 U.S.C. 154(b) by 0 days.

(21) Appl. No.: 16/499,386

(22) PCT Filed: Mar. 29, 2018

(86) PCT No.: PCT/EP2018/058119
§ 371 (c)(1),
(2) Date: Sep. 30, 2019

(87) PCT Pub. No.: WO2018/178257
PCT Pub. Date: Oct. 4, 2018

(65) Prior Publication Data
US 2021/0076931 A1   Mar. 18, 2021

(30) Foreign Application Priority Data

Mar. 31, 2017 (FR) .................................. 1752812

(51) Int. Cl.
*A61B 3/11* (2006.01)
*A61B 3/14* (2006.01)
*A61B 3/06* (2006.01)

(52) U.S. Cl.
CPC ............ *A61B 3/112* (2013.01); *A61B 3/066* (2013.01); *A61B 3/145* (2013.01)

(58) Field of Classification Search
CPC .......... A61B 3/066; A61B 3/112; A61B 3/145
(Continued)

(56) References Cited

U.S. PATENT DOCUMENTS

| 5,141,305 | A | * | 8/1992 | Young | ............... | A61B 3/112 351/243 |
| 2009/0213329 | A1 | | 8/2009 | Kandel et al. | | |
| 2015/0245766 | A1 | | 9/2015 | Rennaker et al. | | |

FOREIGN PATENT DOCUMENTS

WO   2015/063598 A1   5/2015
WO   2015/120438 A1   8/2015
(Continued)

OTHER PUBLICATIONS

Binda, P., Straßer, T., Stingl, K. et al. Pupil response components: attention-light interaction in patients with Parinaud's syndrome. Sci Rep 7, 10283 (2017). https://doi.org/10.1038/s41598-017-10816-x (Year: 2017).*

(Continued)

*Primary Examiner* — Zachary W Wilkes (74) *Attorney, Agent, or Firm* — W&C IP (57) ABSTRACT

Evaluation of the perception of colors by mammals with a view to obtaining a characteristic biomarker of each tested subject takes advantage of the slow pupillary oscillatory response to generate an objective neurological signature of this perception of colors. A method based on pupil frequency tagging is used at a tagging frequency $F_{tag}$ adapted to the pupil response speed. A dynamic two-color stimulus is displayed, this stimulus comprising a two-color pattern the colors of which are inverted at the frequency $F_{tag}$, one of the colors gradually varying in a range of possible values. From the pupillary response, a signal representative of the oscillation power of the pupil is generated. The minimum of this signal corresponds to the relative iso-luminance of the tested pair of colors.

22 Claims, 6 Drawing Sheets

(58) Field of Classification Search
USPC .................................................. 351/209, 246
See application file for complete search history.

(56) References Cited

FOREIGN PATENT DOCUMENTS

| WO | 2016/099402 A1 | 6/2016 |
|---|---|---|
| WO | 2018/178258 A1 | 10/2018 |

OTHER PUBLICATIONS

Corinne F. Carle, Andrew C. James, Ted Maddess; The Pupillary Response to Color and Luminance Variant Multifocal Stimuli. Invest. Ophthalmol. Vis. Sci. 2013;54(1):467-475. doi: https://doi.org/10.1167/iovs.12-10829 (Year: 2013).*

Wang CA, Boehnke SE, Itti L, Munoz DP. Transient pupil response is modulated by contrast-based saliency. J Neurosci. Jan. 8, 2014;34(2):408-17. doi: 10.1523/JNEUROSCI.3550-13.2014. PMID: 24403141; PMCID: PMC6608151 (Year: 2014).*

Gamlin, Paul D.R, et al. "Pupil Responses to Stimulus Color, Structure and Light Flux Increments in the Rhesus Monkey." Vision Research, vol. 38, No. 21, 1998, pp. 3353-3358., doi:10.1016/s0042-6989(98)00096-0 (Year: 1998).*

P Cavanaugh et al., "Screening for Color Blindness Using Optokinetic Nystagmus", Investigative Ophthalmology & Visual Science, Apr. 1984, vol. 25, No. 4, pp. 463-466.

A Chaudhuri et al, "A new technique for estimating chromatic isoluminance in humans and monkeys", Visual Neuroscience, 1990, vol. 5, pp. 605-608.

* cited by examiner

*46: Amplitude $A_i$ or DFFT $P_{i,tag}$ at $t_i$

FIG. 5

BIOMARKER OF THE COLOUR PERCEPTION OF A MAMMAL SUBJECT BASED ON PUPIL FREQUENCY TAGGING

FIELD OF THE INVENTION

The present invention relates to the evaluation of the perception of colors by mammals, and more particularly to a method and system for generating an indicator or biomarker of the perception of colors by a mammal subject, such as a human being or an animal.

CONTEXT OF THE INVENTION

The perception of colors is highly variable from one mammal subject to another.

This variability is conventionally explained by different concentrations, distributions and sensitivities, between subjects, of the chromatic photoreceptors (cones) in the solicited zones of the retina, generally in and about the fovea.

The perception of colors varies with the age of the subject.

It is also degraded by dysfunctions related to a genetic or acquired pathology of the eye (the chromatic photoreceptors), of the optical pathways or of the visual cerebral areas.

The evaluation of the perception of colors is useful for many both medical and non-medical applications.

By way of example, document US 2015/245766 uses the difference in pupillary response of a patient to white (or red) and blue flashes to determine a neurological deterioration of the patient.

One method, called the chromatic iso-luminance method, consists in determining when all (generally both) of the colors of a combination of colors, one of which varies over time, are perceived by the subject to have the same luminance. This evaluation is widely used in psychophysical and neurophysiological studies of visual processing by mammals. It in particular allows the integrity of the perception of colors by the subject to be evaluated, but also the relative contribution of the cells sensitive to luminance in the perception of colors to be isolated.

For a long time, the evaluation of chromatic iso-luminance has remained subjective because it is based on perceptual judgements by subjects.

In order to allow an objective evaluation of mammal subjects that are unable to communicate verbally, such as animals and babies, indicators or biomarkers of the perception of colors by a mammal subject have been created. These indicators or biomarkers are in some respects objective neurological and physiological signatures of the perception of the tested colors.

The publication "Screening for color blindness using optokinetic nystagmus" (Cavanagh P. et al., 1984) for example describes the generation of a signal representative of the nystagmus of the eye of the subject in response to an illusory scintillation in a grid formed of red and green bars, one of the colors gradually being modified over time. This response signal is an indicator of the perception of colors by the tested subject. In particular, the iso-luminance between the two tested colors (red and green) is obtained at the moment at which the direction of movement of the eye inverts in the nystagmus signal.

The publication "A new technique for estimating chromatic isoluminance in humans and monkeys" (Chaudhuri A. et al., 1990) also discloses generating an opto-kinetic signal in response to the display of a dynamic two-color stimulus. A change in direction of the nystagmus is also used to identify the iso-luminance between the two colors (green and grey) used.

These techniques based on the opto-kinetic response of subjects as indicator of the perception of colors however require a very precise analysis of the movement of the eyes. Specifically, the involuntary oscillations of the eyes in response to the dynamic two-color stimulus are generally abrupt and rapid. Sophisticated image-acquiring devices (for example 100 images/second video cameras) and high-performance processing means, in particular for real-time processing, are therefore required.

Furthermore, in order to guarantee this precision, it is necessary for the gaze of the subject not to move. This constraint is difficult to meet with certain subjects, such as animals and babies.

In addition, the use of a gaze-tracking device to measure ocular movements requires the gaze-tracking device to be calibrated. The calibration procedure also requires a response from the subjects, making these measurements difficult on uncooperative subjects.

There is thus a need for indicators or biomarkers of the perception of colors that are simple to obtain and less constraining.

SUMMARY OF THE INVENTION

The inventors have had the idea of exploiting the response of the pupil to luminance variations. Specifically, since this response (contraction or dilation of the pupil) is slower than nystagmus, the inventors concluded that less sophisticated equipment and processing operations would then be sufficient.

In this context, the present invention firstly relates to a method for generating an indicator or biomarker of the perception of colors by a mammal subject, comprising the following steps:

subjecting the mammal subject to at least one dynamic multi-color, typically two-color, stimulus comprising displaying, on a display peripheral (screen or any other visual medium), a multi-color, typically two-color, pattern at least two colors of which are periodically inverted at a frequency called the tagging frequency. The multi-color pattern thus displays a plurality of colors (including the two that invert) at each given time, controlling a modification over time of at least one of the two colors of the multi-color pattern during the display of the dynamic multi-color stimulus, in order to make the display luminance of this color vary (generally several times). The modification of the color is intended to make the relative luminance of the two colors (i.e. a real or perceived luminance difference) vary over time, acquiring, with an image-acquiring device, an oscillatory response of at least one pupil of the mammal subject, during the display of the dynamic multi-color stimulus, and generating, from the acquired response, a signal representative of the power of the oscillatory response of the pupil as a function of the modification over time of at least one of the two colors (and more generally a luminance difference between the two colors) during the display of the dynamic multi-color stimulus.

Conventionally, the oscillatory response of the pupil consists in measuring the variation (constriction and dilation) of the diameter of the pupil over time. Advantageously, the pupils of the two eyes may be analyzed separately or in combination (for example by way of an average).

Because of the slow oscillatory response of the pupil, the tagging frequency used is quite low and, in addition, far from other physiological frequencies of the subject.

Because of this farness from physiological frequencies, the signal/noise ratio of the oscillatory response of the pupil is naturally high. It then allows a signal representative of the power of the oscillatory response that truly represents the pupillary response, without contamination, to be obtained. This signal representative of the retinal response and/or relative (specific to the subject) perception of the tested colors may therefore serve directly or be related directly to a reliable indicator or biomarker of the discrimination and/or perception of colors.

The generated signal may then be used in medical or non-medical applications, as mentioned below, and for example in order to determine a chromatic iso-luminance between two tested colors.

Furthermore, by use of a low tagging frequency, generally of about 0.1 Hz to 5 Hz, and for example of 1.3 or 1.4 Hz, conventional video-acquiring devices, typically 25 images-per-second video cameras (such as those with which computers and cell phones are equipped), are sufficient. The in particular real-time processing of the acquired signals is then substantially less resource intensive.

Correlatively, the invention relates to a system for generating an indicator or biomarker of the perception of colors by a mammal subject, comprising:

a display peripheral, a computational system for stimulating the mammal subject with a dynamic multi-color, typically two-color, stimulus, the computational system controlling the display, on the display periphery, of a multi-color, typically two-color, pattern at least two colors of which are periodically inverted at a frequency called the marking frequency, a color controller configured to modify over time at least one of the two colors of the multi-color pattern during the display of the dynamic multi-color stimulus, in order to make the displayed luminance of this color vary, an image-acquiring device for acquiring an oscillatory response of at least one pupil of the mammal subject, during the display of the dynamic multi-color stimulus, and an indicator or biomarker generator configured to generate, from the acquired response, a signal representative of the power of the oscillatory response of the pupil as a function of the modification over time of at least one of the two colors during the display of the dynamic multi-color stimulus.

This system has advantages similar to those of the method described above.

Optional features of the method according to the invention are moreover defined in the dependent claims. The system according to the invention may also comprise means configured to implement these optional features.

In one embodiment, the method furthermore comprises a step consisting in determining the iso-luminance two-color configuration of the two colors (i.e. the values of these two colors) of the dynamic multi-color stimulus corresponding to a minimum of the signal representative of the power of the oscillatory response of the pupil. The inventors have observed that because of the periodic inversion of the two colors in the pattern, the pupil oscillates at the corresponding (tagging) frequency with a response that increases in power as the perceived intensity differential between the two colors increases. Thus, determining the minimum of the signal representative of the power makes it possible to determine the chromatic iso-luminance perceived by the subject for the two tested colors, i.e. to determine when the luminance difference that is made to vary over time between the two tested colors is minimum as perceived by the subject. The chromatic iso-luminance correspondence may be used as indicator or marker of the perception of color by a subject. Specifically, it may be compared to that obtained for other subjects.

The computations employed to determine the chromatic iso-luminance are excessively simplified with respect to known techniques. Furthermore, the position of the minimum in the signal representative of the power is independent of the unit used to measure the oscillatory response of the pupil. Thus, this configuration allows a calibration of the image-acquiring device to be avoided.

In one embodiment, the other color among the two colors of the multi-color pattern is kept fixed during the display of the dynamic multi-color stimulus.

In another embodiment, the tagging frequency is dependent on the subject. In particular, the method may furthermore comprise a prior step of determining the tagging frequency, comprising subjecting the subject to at least one calibrating light flash, measuring an average response time of the pupil of the mammal subject to the calibrating light flash, and setting the tagging frequency depending on the measured average response time.

These arrangements in particular make it possible to improve, at low time cost, the reliability of the measurements carried out, and for example the chromatic iso-luminance configuration for the tested colors. Furthermore, they allow the duration of the test (submission to the dynamic multi-color, typically two-color, stimulus) to be optimized and in particular decreased.

As a variant or in combination, the multi-color pattern used is dependent on the subject, for example dependent on the oscillatory response of the pupil to light flashes. This in particular allows a potential pathology of the subject that decreases the spatial sensitivity of the eyes of the subject to be taken into account. By way of example, the multi-color pattern may be positioned in a preferential zone of the screen given the subject, for example the top or bottom of the screen, or even one particular quarter of the screen.

In one embodiment, the control of the modification over time of the color comprises a gradual modification in increments (or steps). This allows stable oscillatory responses, in particular in a moving analysis window, to be acquired. In particular, a frequency of modification (in increments) of the color is smaller than the tagging frequency. Preferably, the modification frequency of the color is a sub-multiple of the tagging frequency. This makes it possible to obtain a plurality of alternations of the same two colors in the multi-color, typically two-color, pattern displayed and therefore to acquire a better quality oscillatory response.

In one embodiment, the mammal subject is subjected to two successive dynamic multi-color, typically two-color, stimuli based on two different pairs of colors. This measure allows a complete relative indicator of the perception of colors by the subject to be obtained. Specifically, the color space is generally three-dimensional (for example RGB, for red-green-blue) such that knowledge of the relative perception of two pairs of colors allows (via simple computations for example) the relative perception of all of the pairs of colors to be deduced. This relative perception is for example the chromatic iso-luminance correspondence.

In one embodiment, the display of colors on the display peripheral is controlled using triplets of red-green-blue values, and the two colors of the multi-color pattern are pure colors for which two of the three red, green, blue components are zero. Thus, the modification over time of the color is achieved simply by gradually incrementing the non-zero third component.

In this case, the two pairs of colors indicated above are chosen, in the RGB space, from the pairs RG, RB and GB, where R, G, B are the colors pure red, pure green and pure blue, respectively.

The signal representative of the power may be formed in various ways depending on the processing applied to the acquired response signal.

In a first embodiment, the signal is a signal representative of the oscillation power of the pupil at the tagging frequency and/or at one or more of its harmonics, representative of the variation in the frequency component, at said tagging frequency and/or one or more of its harmonics, of the oscillatory response of the pupil. By "harmonics" what is meant is multiples and/or sub-multiples of the tagging frequency. Typically, apart from the tagging frequency $F_{tag}$, the half-harmonic $F_{tag}/2$ and/or the double harmonic $2*F_{tag}$ may be of interest.

Passage to the frequency domain improves the resistance of the indicator or biomarker thus generated, to noise. For example, the generation of the signal representative of the oscillation power of the pupil at the tagging frequency comprises applying, to the acquired response, a discrete fast Fourier transform in a moving time window and storing in memory, for each time window, the value of the frequency component at the tagging frequency and/or at one or more of its harmonics of the obtained frequency spectrum. These processing operations may advantageously be carried out in real-time, with little in the way of memory resources.

In particular, the width of the moving time window is chosen to be at least equal to the period associated with the tagging frequency, and for example to at least twice this period.

According to another particular feature, the moving time window is shifted by one sample of the acquired response, on each new application of the discrete fast Fourier transform. The temporal precision of the samples generally depends on the image-acquiring device used and on its configuration. Advantageously, the present invention allows a sampling frequency of 25 Hz, corresponding to the definition of a conventional video camera (25 images per second), to be used. Thus, by virtue of the above measure, the generated signal representative of the oscillation power has the best possible definition given the acquiring device used.

In one particular embodiment, the generation of the signal representative of the oscillation power of the pupil at the tagging frequency and/or at one or more of its harmonics furthermore comprises approximating a signal formed from the values stored in memory of the frequency component at the tagging frequency and/or one or more of its harmonics by at least one mathematical function, for example a piecewise function that may combine one or more sub-functions among an affine function and an exponential function. Conventional techniques for approximating and selecting each sub-function best for one portion of the signal formed from the values stored in memory may be used. Use of such an approximation allows a relatively simple indicator or biomarker to be obtained, and therefore the subsequent processing to be simplified: for example use of this indicator to personalize computational operations or to evaluate the progress of a pathology or the effectiveness of a treatment against such a pathology.

In a second embodiment, the generation of the signal representative of the power comprises determining an amplitude of variation in the diameter of the pupil in response to each inversion of the colors of the multi-color, typically two-color, pattern, said signal representative of the power being formed from the amplitudes thus determined. Specifically, these amplitudes, i.e. the differences in diameter of the pupil in each pupillary response, are representative of the power of the pupillary response, to within a coefficient (the response time of the pupil).

Any other method allowing a signal representative of the power of the oscillatory response (i.e. the response to each controlled change in the display of the multi-color pattern) of the pupil may be used.

On the whole, these analyzing methods may be carried out without particular prior filtering. Moreover and advantageously, the present invention allows a sampling frequency of 25 Hz, corresponding to the definition of a conventional video camera (25 images per second) to be used. Thus, the signal representative of the oscillation power is generated with the best definition possible given the acquiring device used.

In one embodiment, the method may furthermore comprise determining the minimum of the thus generated signal representative of the power, for example the minimum of the piecewise function constructed above or the minimum of the signal of the amplitudes of oscillation of the pupil. This minimum then allows the perceived iso-luminance multi-color, typically two-color, configuration (or the iso-luminance multi-color configurations if for example the pattern includes a plurality of pairs of colors the luminance of one thereof being modified over time) to be identified.

In one embodiment, the method furthermore comprises a step of filtering the acquired oscillatory response, the filtering step comprising interpolating, preferably linearly, an oscillatory response signal during a blink of the eye. This allows point artefacts in the curve to be corrected.

Many pathologies lead to a degradation of the perception of colors by mammals. There is a need for effective indicators or biomarkers of these pathologies. In this context, the invention also relates to a method for determining an indicator or biomarker characteristic of a pathology of a mammal subject, comprising the following steps:

generating a least two indicators or biomarkers of the perception of colors by the mammal subject at two separate respective times, using the method described above while using the same dynamic multi-color stimulus (i.e. for example the same two colors that invert, the same tagging frequency, etc.), and determining an indicator of modification between the two thus generated signals representative of power.

Specifically, the inventors have observed that degradations in the perception of colors related to these pathologies directly degrade (and therefore modify) the signals representative of the power of the oscillatory response of the pupil at the two test times. They then had the idea of establishing a characteristic indicator of these pathologies on the basis of the variation, over time, in these signals representative of the pupillary oscillation power.

This modification indicator, i.e. the indicator or biomarker characteristic of a pathology, may thus be used in a more specific process for detecting a pathology, for tracking a pathology, for tracking the effectiveness of a treatment against a pathology, etc.

Moreover, the two eyes of the subject in question generally do not perceive colors in the same way. The difference in perception may be slight or significant. Provision may therefore be made to obtain such a modification indicator for each of the two eyes. Specifically, certain types of pathologies (certain neurological diseases for example) may be detected when the two indicators are significant, whereas other types of pathologies, more local in effect (ophthalmological diseases such as glaucoma or a retinal disease, but also certain neurological diseases such as multiple sclerosis), may be detected when a single of the indicators (that of the affected eye) is significantly degraded. In particular, for neurological diseases such as multiple sclerosis, the indicator thus generated allows which eye has been affected by the disease to be identified.

Correlatively, the invention relates to a system for determining an indicator or biomarker characteristic of a pathology of a mammal subject, comprising:

a system for generating an indicator or biomarker of the perception of colors by a mammal subject, such as defined above, and a processing module configured to determine an indicator of modification between two signals representative of power that are generated, by the generating system, at two separate times for the same subject using the same dynamic multi-color stimulus.

Optional features of the method for determining an indicator or biomarker according to the invention are moreover defined in the dependent claims. The system according to the invention may also comprise means configured to implement these optional features.

In one embodiment, the modification indicator includes a difference between the average values of the two thus generated signals representative of power.

Preferably, the step of generating at least two indicators or biomarkers comprises determining, for each of the two times, the iso-luminance two-color configuration (i.e. the values of the two inverted colors) of the dynamic multi-color stimulus corresponding to a minimum of the thus generated signal representative of the power, and the modification indicator comprises a difference between the color values of the two two-color configurations determined.

Such an indicator or biomarker is simple to obtain, without excessive effort being required on behalf of the tested subject. It allows a degradation in the perception of colors, and therefore a degradation in the eye (chromatic photoreceptors), in the optical pathways (optical nerve) or in visual cerebral areas to be detected.

Thus, this indicator or biomarker allows pathologies such as, non-exhaustively, multiple sclerosis, hepatitises (the short-circuit of the liver possibly being accompanied by a neurological degradation due to intoxications), diabetes (also possibly accompanied by a neurological degradation), neurodegenerative diseases (Alzheimer's, Parkinson's), neurodevelopmental diseases (schizophrenia, autism), neurovascular diseases (stroke), intoxications (affecting the neurological system), age-related macular degeneration, glaucoma and retinal diseases, etc. to be diagnosed but also the progression thereof to be tracked.

In this context, the invention also relates to the use of the modification indicator obtained for a mammal subject using the above method for determining an indicator or biomarker characteristic of a pathology of a mammal subject to diagnose a pathology or to track the progress of a pathology of the subject.

This use may in particular comprise comparing the modification indicator with a threshold value. By way of example, if the chromatic iso-luminance difference between two measurements carried out (the two two-color configurations minimizing the signal representative of the oscillation power) is large (greater than the threshold value), this may mean that the neurological system of the subject is degraded, and that thus a curative treatment in the process of being trialed is ineffective, or in contrast that the neurological system of the subject has improved (if the difference shows a return to a more normal iso-luminance configuration). Of course, the threshold value may be adjusted depending on the difference between the two measurement times, but also depending on the tracked pathology and the subject in question.

BRIEF DESCRIPTION OF THE FIGURES

Other details and advantages of the invention will become further apparent from the description below, which is illustrated by the appended drawings, in which.

DETAILED DESCRIPTION OF EMBODIMENTS OF THE INVENTION

The present invention relates to the perception or discrimination of colors by mammals with a view to forming therefrom a biomarker characteristic of each tested subject. It takes advantage of the slow pupillary oscillatory response (between 0.1 Hz and 5 Hz) of a mammal subject to an oscillatory light stimulus to generate an objective neurological signature of the relative perception of colors by a subject.

A pupil frequency tagging method is used at a tagging frequency $F_{tag}$ that is adapted to the pupillary response speed, and that advantageously is far from other physiological frequencies associated with the response movements of the eye of the subject. By way of example, $F_{tag}$ is about 1.3 to 1.4 Hz or less.

This method is robust to the noise resulting from other eye movements of the subject and does not require calibration on the part of the subject.

This method for example allows the chromatic iso-luminance perceived by a subject to be determined from the obtained neurological signature.

Figure 1:
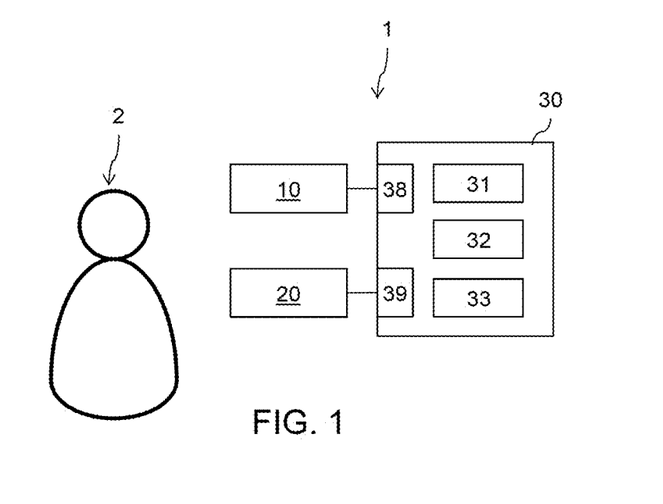
FIG. 1 illustrates a system for generating an indicator or biomarker of the perception of colors by a mammal subject according to one embodiment of the invention.

FIG. 1 illustrates a system 1 for generating an indicator or biomarker of the perception of colors by a mammal subject 2.

It comprises a display screen 10, an image-acquiring device 20 and a processing and controlling computational system 30.

The display screen 10 is a panel of pixels, for example of 1920×1080 pixel resolution with a display frequency of for example 60 Hz, driven by a video card of the system 30. Each pixel is formed from three red, green and blue (RGB) color components each of 8 bits (i.e. able to take values from 0 to 255). Of course, other pixel definitions (number of bits per color, color space) may be envisioned in the context of the present invention.

The screen 10 may be positioned centered facing the eyes of the subject, in a plane perpendicular to the gaze, and at a fixed distance from the subject 2. In order to avoid any movement of the subject 2, the head of the latter may be stabilized by making it rest via the chin and forehead on and against suitable rests.

The image-acquiring device 20 is typically a video camera sensitive to infrared or any other type of sensor allowing a pupillary diameter to be recorded, said video camera also being placed facing the subject in order for it to be able to acquire images of one or more pupils of the subject 2.

For reasons of simplification of the explanations, the acquisition of images will be limited below to a single pupil of the subject 2. Of course, similar processing may be carried out on the acquisition of images of both pupils: for example averages may be taken or the results obtained for one pupil corroborated with the results of the other pupil, or lastly the degradation of one pupil relative to the other may be analyzed.

On account of the relatively low tagging frequency $F_{tag}$, the use of off-the-shelf video cameras 20, of 25 images/second type, is possible. In particular the video cameras found in conventional electronic devices (cell phones, computers, tablets, portable video cameras) may be used provided that they are sensitive to the infrared.

Of course, video cameras having acquisition frequencies higher than 25 im/s may also be used.

When a video camera operates in a wider frequency spectrum than that of the infrared, provision may be made for (physical or electronic) filtering using known techniques (that are not described here) in order to obtain, at the end of the acquisition, solely images in the infrared spectrum or at the very least to allow the diameter of the observed pupil to be determined.

The controlling and processing computational system 30 comprises a computational module 31 for stimulating the mammal subject by dynamic multi-color, typically two-color, stimulus, a color controller 32 and an indicator or biomarker generator 33. These various elements are implemented by software because it is essentially a question of processing operations aiming to control a display on the screen 10 or to process data acquired by the device 20. To this end, the system 30 also comprises a conventional video card 38 to which the screen 10 is connected, and a conventional video-acquisition card 39 to which the acquiring device 20 is connected.

The system 30 may furthermore comprise input/output means (keyboard, mouse, network card) in order to allow an operator to parameterize the system and to trigger the processes and applications of the invention.

The computational module 31 for stimulating the mammal subject by dynamic multi-color, typically two-color, stimulus controls the display, on the screen 10, of a multi-color, typically two-color, pattern at least one of the two colors of which are periodically inverted at the tagging frequency $F_{tag}$.

The multi-color pattern in question displays a plurality of colors each given time. At least two of these colors are then mutually inverted periodically.

Figure 2:
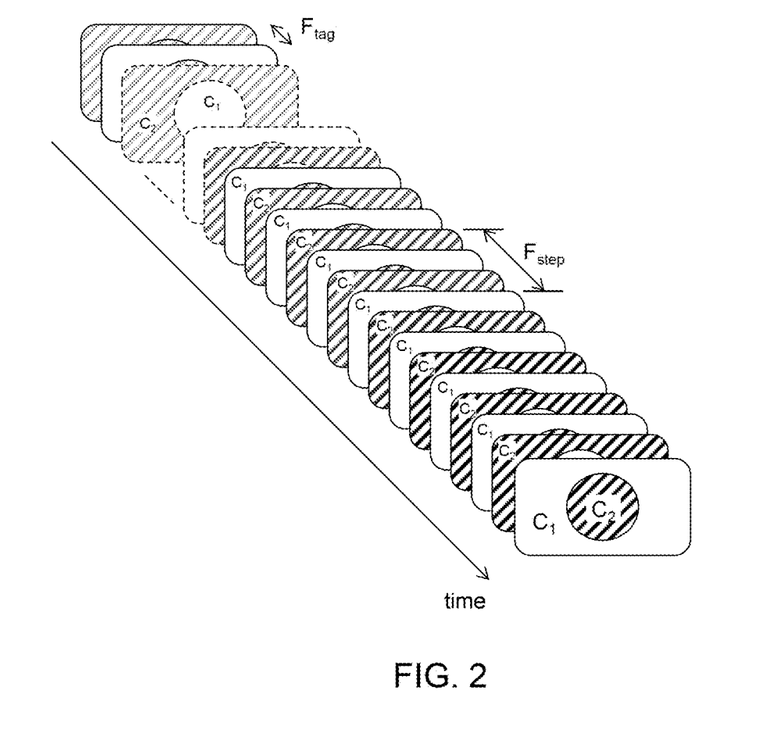
FIG. 2 schematically illustrates a dynamic two-color stimulus according to one embodiment of the invention.

FIG. 2 schematically illustrates an example of a two-color pattern formed from the colors $C_1$ and $C_2$, namely a uniform screen background of one of the colors (here left white for better readability) with, at its center, a uniform circle of the other color (here hatched for better readability). The dynamic two-color stimulus consists in creating an alternation between the two colors $C_1$ and $C_2$ at the frequency $F_{tag}$. The two-color pattern may be present on a white background for example.

Preferably, the two colors $C_1$ and $C_2$ of the two-color pattern are pure colors, i.e. colors for which two of the three red, green, blue components are zero. In the RGB color space, $C_1$ and $C_2$ are thus either RG, or RB, or GB, where R, G, B are the colors pure red $(r_i, 0, 0)$, pure green $(0, g_i, 0)$ and pure blue $(0, 0, b_i)$, respectively.

It will be noted that $C_1$ and $C_2$ may be chosen to be the same pure color (RR, GG, BB), in particular for inspection tests. Of course, other choices of pairs of colors $(C_1, C_2)$ not necessarily involving pure colors may be envisioned.

The color controller 32 is configured to modify over time at least one of the two colors of the multi-color, typically two-color, pattern (FIG. 2) during the display of the dynamic multi-color, typically two-color, stimulus on the screen 10, in order to make the displayed luminance of this color vary (generally a plurality of times). For pure colors, the luminance variation is easy to obtain, consisting simply in modifying the single non-zero component ($r_i$ or $g_i$ or $b_i$).

This modification of one of the two colors has the objective of making the relative luminance of the two colors in question vary over time, i.e. of making a luminance difference between the two colors, which difference may be real or perceived by the subject, vary.

In one embodiment, the other color of the pattern, let's say $C_1$, is kept fixed during the display of the dynamic two-color stimulus. This means that, throughout the test (all of the displayed images of FIG. 2), the color $C_1$ is displayed with the same RGB triplet. Of course, this other color may also be modified over time (for example in the contrary sense to the first color). What is important here is to determine the shift between the two colors that ensures a perceived iso-luminance. To a first approximation, this shift may then be applied to any value of one of the colors, to obtain the value of the other color in iso-luminance configuration.

The modification over time in the color $C_2$ is preferably achieved in steps that increase in a range of possible values (for example from 0 to 255 for the single modified component) or in a range of values to be tested, or in steps that decrease (for example from 255 to 0) during the test. For impure colors, the resulting luminance (various formulae based on RGB components are known to those skilled in the art) will be chosen to increase or decrease during the test.

As a variant, a modification of the color $C_2$ by dichotomy about a first iso-luminance value set in a first test (based on the techniques of the present invention or using other methods) may be envisioned.

Other examples of multi-color patterns, for example a pattern including a higher number of colors or a multi-color pattern displaying two or more different pairs of colors that are inverted pairwise as explained for example above, may be used. Also, spatially different patterns may be envisioned in the display zone on the screen 10, for example a display on any of the quarters of the screen or indeed even a display on the top (or right-hand) or bottom (or left-hand) part of the screen.

To simplify the explanations that follow, reference is mainly made to a two-color pattern the two simultaneously displayed colors of which are inverted (which pattern may for example be displayed on a uniform background, resulting in a multi-color display).

FIG. 3a illustrates an example of control of the modification over time in the color $C_2$ consisting in a gradual modification in increments (staircase). The luminance difference between the two colors thus varies over time. In this example, the non-zero component of the color $C_2$ is made to vary between 20 and 220 (the extremes are not significant), in steps of 20 units. Of course, other tested ranges, with other step sizes may be used to decrease or increase the duration of the test, but also to decrease or improve the precision of the determination for example of the chromatic iso-luminance.

In particular, a higher precision (narrower range and smaller steps) may be used, in a second test, about an approximative iso-luminance value (i.e. the value of $C_2$ having the same luminance as perceived by the subject 2 as the fixed value of $C_1$) determined beforehand in a first test (based on the techniques of the present invention or using other methods).

As illustrated in FIG. 2, the frequency $F_{step}$ of incrementation of the value of $C_2$ is chosen to be lower than the tagging frequency $F_{tag}$, and for example 3 times lower (FIG. 2—meaning that three consecutively displayed images have a color $C_2$ of same value) or about 10 (FIG. 3a) or even more times lower, or optionally a sub-multiple of $F_{tag}$.

Figure 3:
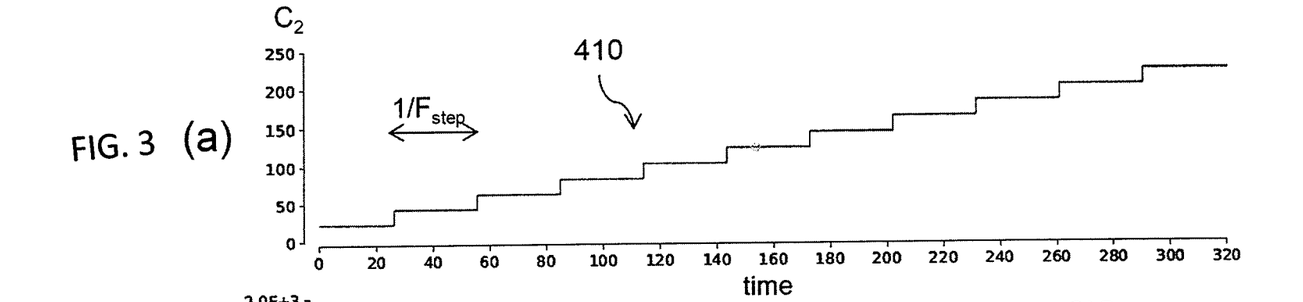
FIG. 3a illustrates a modification pattern or profile of one of the colors of the two-color pattern of the stimulus of FIG. 2 according to one embodiment.
FIG. 3b shows an example of an oscillatory response of a pupil in response to a dynamic two-color stimulus of the type shown in FIG. 2 according to one embodiment.
FIG. 3c schematically illustrates a frequency spectrum resulting from the application of a discrete fast Fourier transform to an analysis window of the signal of FIG. 3b according to one in embodiment.
FIGS. 3d and 3d' illustrate signals representative of the oscillation power of the pupil, and a piecewise function approximating them, according to various embodiments.
FIG. 3e illustrates the determination of a chromatic iso-luminance value from the modification profile of FIG. 3a according to one embodiment.
Figure 3C:
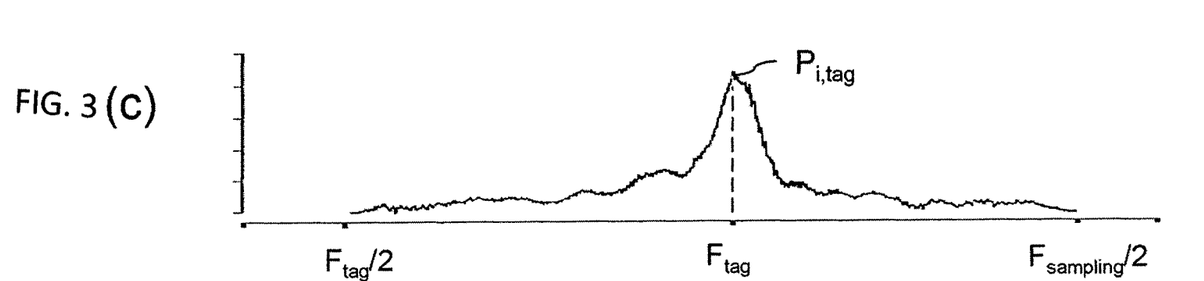
Figure 3D:
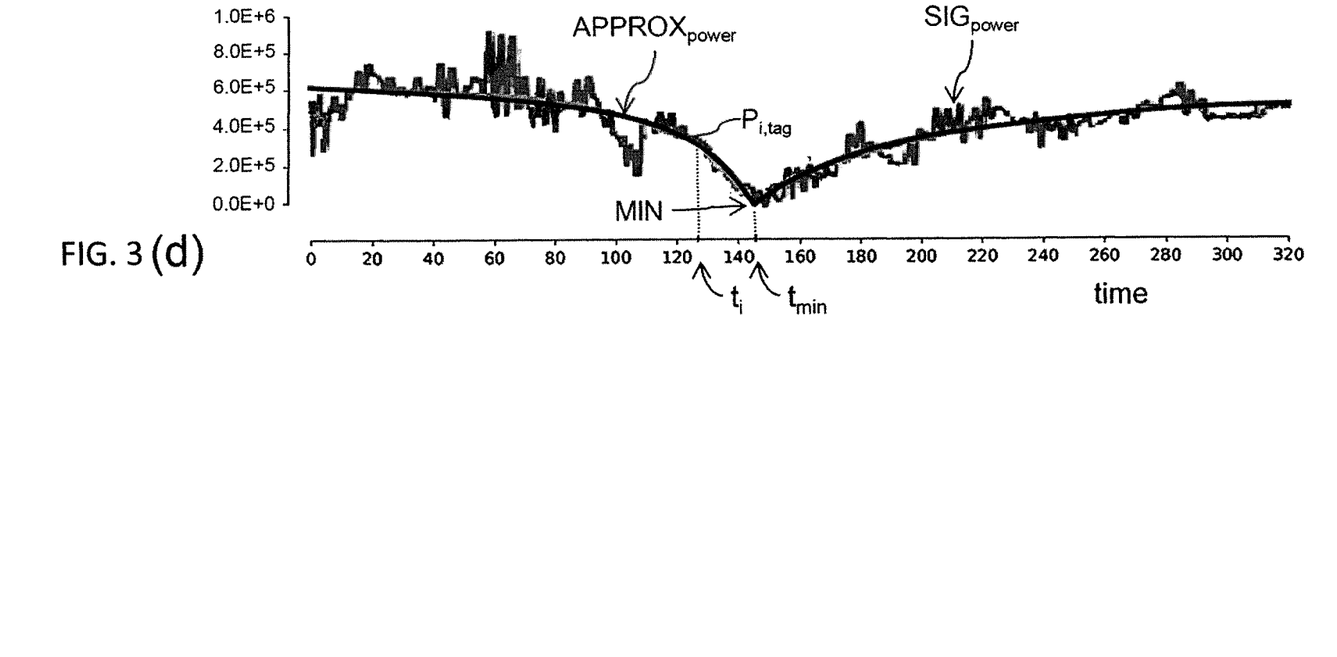

Returning to FIG. 1, the indicator or biomarker generator 33 is configured to generate, from an oscillatory response $SIG_{resp}$ of at least one pupil of the subject 2, which response is acquired by the acquiring device 20, a signal called the pupil oscillation power signal $SIG_{power}$. An example of an oscillatory response is illustrated in FIG. 3b, whereas examples of pupil oscillation power signals are illustrated in FIGS. 3d and 3d'.

This signal $SIG_{power}$ is representative of the power of the oscillatory response of the pupil as a function of the modification over time (FIG. 3a) of at least one of the colors during the display of the dynamic two-color stimulus.

Various embodiments may be envisioned for obtaining this signal $SIG_{POWER}$.

A rapid first method consists in determining an amplitude $A_i$ of variation in the diameter of the pupil in response to each inversion (at $t_i$) of the colors of the two-color pattern. Each amplitude $A_i$ quantifies the modification of the diameter of the pupil during the pupillary response. Such an amplitude is representative of the power of the pupillary response, to within a coefficient (the response time of the pupil). The signal $SIG_{power}$ is then formed from the amplitudes thus determined (see FIG. 3d' in which the triangles schematically represent each determined amplitude $A_i(t_i)$).

A second method that is more resistant to noise consists in working in the frequency domain of the oscillatory response $SIG_{resp}$. In this case, the signal $SIG_{power}$ is preferably a signal representative of the pupil oscillation power at the tagging frequency, which signal is representative of the variation in the frequency component $P_{i,tag}$, at said tagging frequency $F_{tag}$, of the oscillatory response $SIG_{resp}$ of the pupil as a function of the modification over time (FIG. 3a) of the color $C_2$ during the display of the dynamic two-color stimulus (FIG. 2). The signal $SIG_{power}$ is then formed from the frequency components $P_{i,tag}$ thus determined (see FIG. 3d).

It will be noted that the determination of these frequency components does not necessarily require complete oscillatory responses to be acquired on each inversion of the colors. Specifically, known techniques allow these frequency components to be obtained from a partial cycle of the oscillatory response of the pupil. In one preferred embodiment, complete oscillatory responses are employed.

As a variant, or in combination with the first harmonic $F_{tag}$, it is possible to use harmonics of the tagging frequency $F_{tag}$, in particular sub-harmonics such as the half-harmonic $F_{tag}/2$ and/or multiple harmonics such as the double or second harmonic $2*F_{tag}$. In this case, each harmonic is processed separately as described below, their results possibly being combined (by way of an average or to adjust the result of the first harmonic, etc.) in order in particular to obtain a single iso-luminance two-color configuration.

Thus, from the signal $SIG_{power}$ of any processed harmonic, the indicator or biomarker generator 33 may in particular determine the iso-luminance of $C_2$ with respect to $C_1$ (fixed). As explained below with reference to FIG. 4 in relation to FIGS. 3d and 3e, this chromatic iso-luminance corresponds to the iso-luminance two-color configuration of the dynamic two-color stimulus corresponding to a minimum of the signal $SIG_{power}$. Specifically, the amplitude of the pupillary response and therefore its oscillation power closely follow the variations in luminance of the displayed stimulus. They are therefore minimum when the variations in luminance are minimum, i.e. when the displayed two-color pattern is perceived by the subject to have a chromatic iso-luminance.

Figure 4:
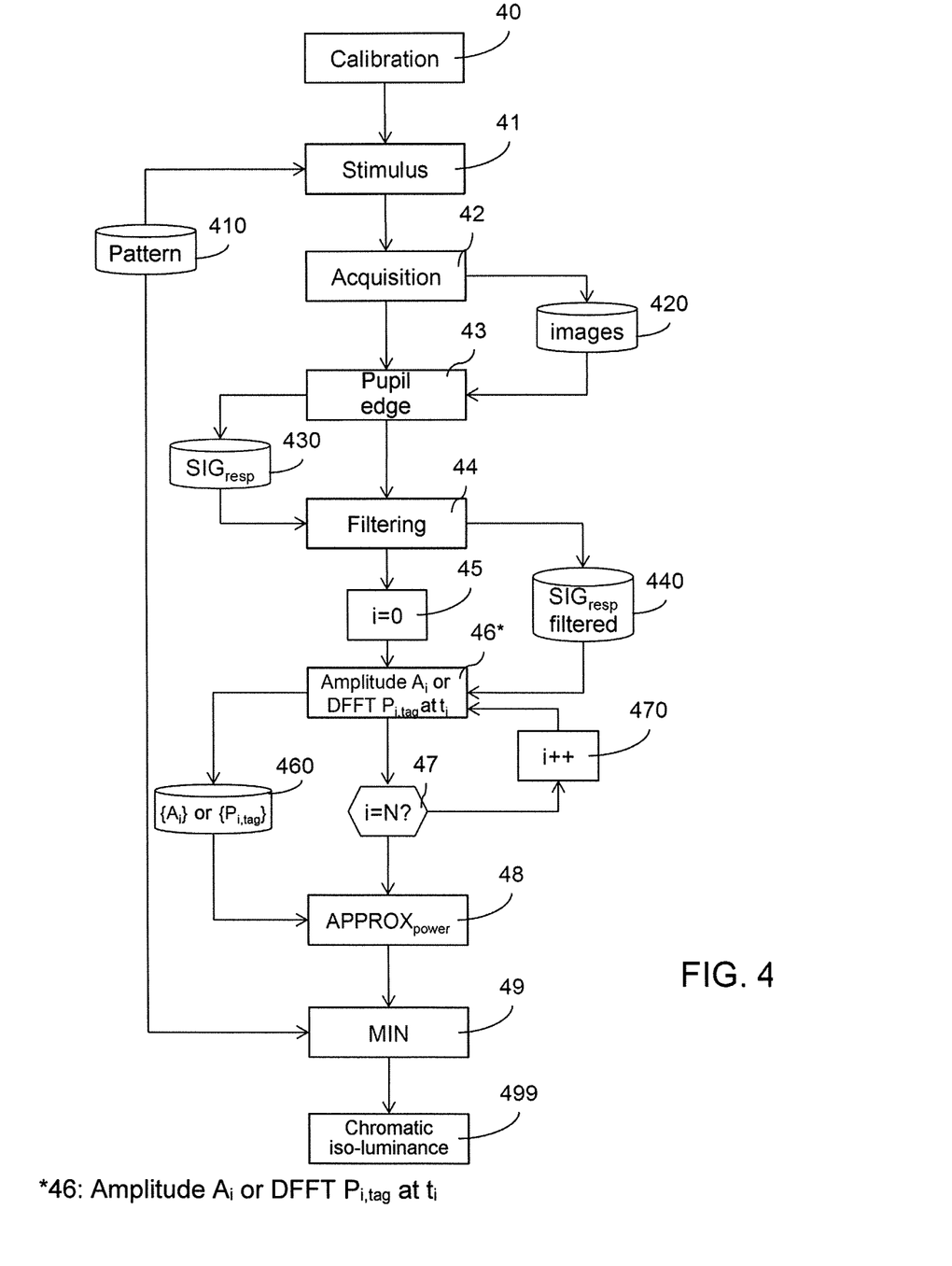
FIG. 4 illustrates, via a flowchart, a method for generating an indicator or biomarker of the perception of colors by a mammal subject according to embodiments of the invention.

With reference now to FIG. 4, an example of a method for generating an indicator or biomarker of the perception of colors by a mammal subject according to the teachings of the invention will be described.

On turn on of the system 1, an optional step 40 allows the system 1 to be calibrated to the tested subject 2. In particular, the aim of this step is to determine the frequency $F_{tag}$ depending on the subject 2 and/or the pattern to be used. Specifically, pupillary response time varies, sometimes greatly, from one subject to the next. Thus, to decrease the duration of the test or to guarantee relevant measurements, it is preferable for $F_{tag}$ to be as high as possible while making sure it does not exceed the pupillary response speed of the subject.

Moreover, a pattern that is spatially differentiated with respect to the point of fixation of the subject may be envisioned in order to isolate symptoms specifically affecting certain zones of the retina of the subject. For example, a top-bottom difference in color perception may exist for patients suffering from Alzheimer's, whereas particular zones are not easily perceived by patients suffering locally from ARMD (these zones corresponding to portions degenerated in the retina on account of the pathology).

The calibrating step 40 generally consists in recording the pupillary response of the subject (generally a constriction), in order to deduce therefrom a pupillary response time and thus a frequency $F_{tag}$ to be used (for example using a lookup table), and/or a zone of better sensitivity of the subject defining a preferred zone of display of the two-color pattern.

By way of example, the subject 2 may be subjected to at least one calibrating light flash controlled by the system 30 and displayed on the screen 10 (for example a screen that suddenly changes to white from dark or a white zone that suddenly appears on a dark screen, the location of this white zone possibly varying during the calibration test).

An acquisition, by the device 20, of images of the pupillary response(s) of the subject 2 (to the flash or to the multiple flashes) allows a signal representative of the variation in (constriction of) the pupil (in particular its diameter) to be obtained, from which the response time (optionally average over a plurality of responses) of the pupil may be measured by conventional techniques (for example the time taken, starting from the flash, to reach 90% of the constriction in response). Conventionally, the pupillary response time of an individual is about 0.5 seconds to 2 seconds.

On the basis of this measured or computed response time, step 40 sets the frequency $F_{tag}$. This may be done using a lookup table (which associates, with ranges of response times, respective values of $F_{tag}$) in order to obtain a limited number of tagging-frequency values. As a variant, the period associated with the tagging frequency $F_{tag}$ may be set to twice the measured response time or to another multiple of the measured response time.

By default, a value $F_{tag}$ of about 1.3 to 1.4 Hz may be used.

Furthermore, on the basis of pupillary responses to the display of a flash in a plurality of zones of the screen, while the subject keeps the same point of fixation, the device determines a zone of best sensitivity of the subject. This zone may then be used to display the two-color pattern on only one portion of the screen. Thus, spatially differentiated patterns are finally displayed depending on the subject in question.

In step 41, the subject 2 is subjected to at least one dynamic multi-color, typically two-color, stimulus.

Although the following description focuses on the submission of the subject to a single two-color stimulus, provision may be made to subject him successively to two successive dynamic two-color stimuli based for example on two different pairs of colors, in order in particular to determine the relative color perception of the subject over all of the three-dimensional RGB color space. By way of example, a test that determines the subject's chromatic iso-luminance for the RG pair may be combined with a subsequent second test that determines the chromatic iso-luminance of the GB pair. The relative perception of the colors red and blue may then be directly deduced, and hence the subject's relative perception of all the colors in the color space is known.

Furthermore, although the stimulus used here is two-color in the sense that only two colors are inverted, one thereof at least varying over time, provision may be made for the multi-color stimulus used to comprise a plurality of different pairs of colors inverted at the frequency $F_{tag}$, said pairs being displayed simultaneously on the same screen.

In step 41, the computational module 31 for stimulating the mammal subject by dynamic two-color stimulus controls the display of the two-color pattern optionally in a preferred display zone and the periodic inversion of the two colors $C_1$ and $C_2$ at the frequency $F_{tag}$ (FIG. 2). At the same time, the luminance of the color $C_2$ is modified over time according to a modification profile 410, under the control of the color controller 32. The modification profile may be incremental as shown in FIG. 3a for the non-zero component of $C_2$.

In step 42, the image-acquiring device 20 films and acquires images, in the infrared spectrum, of the monitored pupil of the subject 2. These images are transmitted to the system 30 and stored in memory 420. The acquisition is carried out at a sampling frequency $F_{sampling}$ of 25 to 1000 images per second, depending on the capacities of the device 20.

In step 43, the acquired images are processed using an algorithm for detecting the edge of the pupil and for measuring the diameter of the pupil. These measurements allow a pupil oscillatory response signal $SIG_{resp}$ to be generated during the display of the dynamic two-color stimulus, this signal representing the variation in the diameter of the pupil over time.

FIG. 3b illustrates an example of a pupil oscillatory response $SIG_{resp}$ to a dynamic red-green two-color stimulus the pure-red color of which is fixed to (140, 0, 0) and the pure-green color of which follows the curve of FIG. 3a ($F_{step}$=0.0345 i.e. steps of about 29 seconds). The frequency $F_{tag}$ is set to 0.345 Hz.

The curve $SIG_{resp}$ thus obtained is stored in the memory 430 of the system 30.

It will be noted that the edge-detection processing operation and the processing operation for generating $SIG_{resp}$ may be carried out by the acquiring device 20 in order to decrease the volume of data to be transmitted to the computational system 30.

The oscillatory response $SIG_{resp}$ may be exploited as is in steps 45 to 49 described below. Specifically, the use of a frequency $F_{tag}$ far from the frequencies of physiological noise guarantees this response is of good robustness.

Provision may however optionally be made to filter this response in particular for the purpose of removing artefacts from the signal.

In this case, the method continues with the optional step 44 of filtering the acquired oscillatory response $SIG_{resp}$. The objective of this filtering step is in particular to remove noise from the signal, for example noise resulting from a blink of the eye (no pupil detectable by the edge-detection algorithm).

In one embodiment, step 44 consists in interpolating, preferably linearly, the oscillatory response signal $SIG_{resp}$ during one or more blinks of the eye, i.e. when the edge-detecting algorithm has been unable to detect a pupil in the images. Conventional interpolation techniques may be used.

By way of example, filtering based on the Savitzky-Golay method may be employed.

The signal thus filtered is preserved in the memory 440 of the system 30.

It is from this optionally filtered signal $SIG_{resp}$ that the signal $SIG_{power}$ is generated.

In the aforementioned first embodiment, the generator 33 may determine the times $t_i$ of inversion of the colors in the displayed two-color stimulus, then determine, in each corresponding oscillatory response, the amplitude $A_i(t_i)$ of the variation in the pupillary diameter of the subject 2.

It may simply be a question of determining the difference between the value of the diameter at the moment of the inversion in color and the opposite extreme value (maximum or minimum) of the diameter in a time window substantially corresponding to the response time of the subject.

Of course, other methods for evaluating amplitude may be envisioned, such as for example use of a percentage of the extreme value of the diameter or the value of the diameter at 90% (or less) of the response.

All of the computed amplitudes, associated with respective times of inversion of the colors, form the signal $SIG_{power}$ (FIG. 3d) used in steps 48 and 49 below.

In the second embodiment based on the frequency domain, the obtained (optionally filtered) signal $SIG_{resp}$ is transformed to the spectral domain with a view to analyzing the variation in the frequency component $F_{tag}$ and/or in its harmonics. To do this, a discrete fast Fourier transform (DFFT) is applied to the signal $SIG_{resp}$ in a moving time window $W_i$. Thus, a frequency spectrum corresponding to the segment of signal analyzed by the window is obtained. Next, for each analysis time window $W_i$, the value $P_{i,tag}$ of the frequency component at the frequency $F_{tag}$ (and/or of one or more harmonics) is stored in memory.

The rest of the description focuses on the frequency component $F_{tag}$. A similar approach may be used to process any harmonic of interest.

FIG. 3b illustrates the analysis time windows $W_i$ used from the first window $W_o$ to the last window $W_N$. In order to ensure the presence of the frequency component at $F_{tag}$ in the spectrum, the width of the moving time window $W_i$ is at least equal to the period $T_{tag}$ associated with the tagging frequency $F_{tag}$. In the example of the figure, a width equal to $2*T_{Tag}$ (or more) has for example been chosen. Thus, from the window $W_o$, centered on $t_0$, a non-zero component $P_{0,tag}$ may be obtained.

Each analysis window $W_i$ is centered on (and therefore associated with) a time $t_i$. Preferably, a window $W_i$ is associated with each sampling time, in order to maximize the resolution of the signal representative of the oscillatory power formed from the values $\{P_{i,tag}\}$. In this case, the moving time window W is shifted by one sample of the acquired response $SIG_{resp}$, on each new application of the fast Fourier transform. Of course, the step size $STEP_W$ of the shift of the analysis window W may be larger than the single sampling period ($T_{sampling}=1/F_{sampling}$) used in this example. A step size $STEP_W$ set to a plurality of sampling periods allows the number of computations and the required memory size to be decreased.

To obtain a signal $SIG_{power}$ representative of the oscillation power of the pupil at the frequency $F_{tag}$, representative of the variation in the frequency component $F_{tag}$ of the oscillatory response $SIG_{resp}$ of the pupil, the method may firstly comprise initializing a variable 'i' to zero (in order to process each sample) in step 45.

Next, the DFFT is applied to the segment of the signal $SIG_{resp}$ defined by the current time window $W_i$ centered on the sample 'i' to be processed (i.e. $t_i$). FIG. 3c illustrates a schematic example of an obtained frequency spectrum. The absence of frequency components below the frequency corresponding to the width of the window $W_i$ and above the half-sampling frequency (Nyquist criterion) will be noted. Harmonic components of $F_{tag}$ may therefore be present.

This graph shows that the frequency component $P_{i,tag}$ at $F_{tag}$ has an excellent signal/noise ratio, because $F_{tag}$ is far from the physiological frequencies of the subject 2 that potentially generate noise. The value $P_{i,tag}$ is obtained and stored in the memory 460. This is step 46.

It will be understood that the DFFT, since it operates on discrete values (samples), will not necessarily produce a frequency component exactly at the frequency $F_{tag}$. Thus, the value $P_{i,tag}$ may be that of the obtained frequency component closest to $F_{tag}$, or a (linear for example) approximation between the two (or more than two) frequency components surrounding $F_{tag}$, or even an average of two or more frequency components surrounding $F_{tag}$.

It will be noted that the use of a sampling frequency $F_{sampling}$ that is as high as possible and/or of a window W of size that is as large as possible increases the number of frequency samples in the spectrum, in particular about $F_{tag}$.

After step 46, it is determined whether all the DFFTs have been carried out (test 47, which checks whether i=N, number of samples to be processed over the test period), otherwise the variable is incremented (step 470) in order to perform the DFFT of the signal in the following window $W_i$.

When the DFFT has been applied in all the windows (i.e. to all the pieces of the response $SIG_{resp}$), the memory 460 contains all of the values $P_{i,tag}$ that will together form the signal $SIG_{power}$ of the pupil at the frequency $F_{tag}$ (see FIG. 3d).

The signal $SIG_{power}$ generated using any one of these methods is already an indicator or biomarker of the perception of colors by the subject 2. Specifically, it is a question of a robust neurological signature of the subject 2. As will be seen below, the analysis of its variation over time may allow a pathology or an aggravation of a pathology to be detected. This is for example the case for multiple sclerosis.

Optional steps 48 and 49 allow this indicator or biomarker to be refined. The general shape of the signal $SIG_{power}$ contains a central zone that is lower than the lateral zones.

In the optional step 48, an algorithm for approximating the signal $SIG_{power}$ is employed in order in particular to make this signal correspond to a mathematical function. In particular, it is sought to make the signal correspond to a piecewise function, in which each piece may correspond to an affine function, an exponential function or any other conventional function.

In the example of FIG. 3d, a piecewise (two-piece) exponential function $APPROX_{power}$ is used to fit the generally decreasing portion of the signal (to the left) and the generally increasing portion of the signal (to the right). Conventional fitting-based approximating techniques may be used, there being no need for them to be detailed here.

The signal $APPROX_{power}$ thus obtained may also be used as indicator or biomarker of the perception of colors by the subject 2.

The step 49, which is also optional, consists in determining the value $c_2$ of the color $C_2$ that minimizes the power signal $SIG_{power}$ or its approximation $APPROX_{power}$. This is done by determining the minimum MIN of the signal $SIG_{power}$ or $APPROX_{power}$, using conventional techniques, and determining the value of $C_2$ at the time $t_{min}$ corresponding to this signal minimum, using the modification profile 410 (FIG. 3a, reproduced in FIG. 3e).

In the present example, the value $c_2(t_{min})=120$ is obtained for $C_2$. In other words, in the example shown, the subject 2 perceives a relative chromatic iso-luminance between pure red and green colors of values $C_1=(140, 0, 0)$ and $C_2=(0, 120, 0)$.

The iso-luminance configuration 499 thus obtained may serve as indicator or biomarker of the perception of colors by the subject 2.

This configuration may be combined with one or more other corresponding iso-luminance configurations determined using one or more harmonics of $F_{tag}$.

It will be noted that in the case where the dynamic multi-color stimulus used comprises a plurality of different pairs of colors that are inverted at the frequency $F_{tag}$, the minimum MIN of the signal $SIG_{power}$ or $APPROX_{power}$ corresponds to an overall iso-luminance configuration of the various pairs of colors, this configuration not specifically corresponding to one iso-luminance configuration for each pair of colors considered separately.

In one embodiment, the obtained iso-luminance configuration may be confirmed by reproducing the test with an inverse modification profile 410 (decreasing in steps from 220 to 20 for example). In particular, an average of the two values $c_2$ obtained in these two tests may be computed to represent the average iso-luminance configuration of the subject 2 for the colors $C_1$ and $C_2$.

The above method was tested on 4 human subjects during 14 sessions of 45 minutes and 7 non-human mammal subjects during a session of 20 minutes. The adopted tagging frequency was 0.345 Hz, suitable for all of the studied subjects. The two-color pattern used was that of FIG. 2, with one color fixed and the other varying in steps (as schematically illustrated in FIG. 3). The flat screen 10, of 1920×1080 pixel definition, 8 bits per color, and 60 Hz was placed at a distance of 67 cm from the subjects.

The inventors indeed observed, for all of the subjects, a maximum decrease in the power of the pupillary oscillations induced by the luminance variations of the stimulus in the iso-luminance configuration of the tested two-color pattern.

Figure 5:
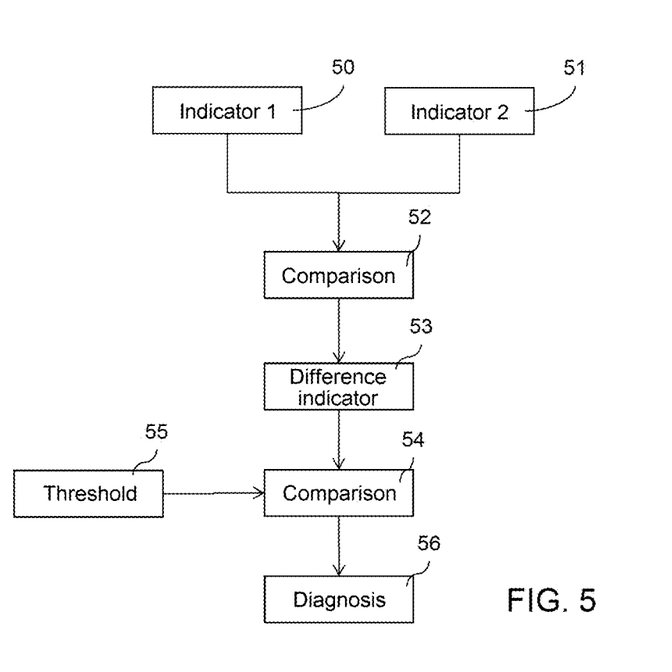
FIG. 5 illustrates, via a flowchart, a method for determining an indicator or biomarker characteristic of a pathology of a mammal subject according to embodiments of the invention.

As will now be seen with reference to FIG. 5, these various indicators or biomarkers may be used for medical purposes, in particular in the determination of an indicator or biomarker characteristic of a pathology of a mammal subject, and therefore are able to be employed in a diagnostic process.

A system for determining an indicator or biomarker characteristic of a pathology of a mammal subject may be similar to the system 1 of FIG. 1 in which a processing module 34 (not shown) is provided and configured to determine an indicator of modification between two signals representative of the oscillation power of the pupil, which signals are generated, by the generating system, at two separate times for the same subject using the same dynamic two-color stimulus.

FIG. 5 illustrates one example of a method for determining an indicator or biomarker characteristic of a pathology of a mammal subject, and its use in a diagnostic process.

The method comprises generating at least two indicators or biomarkers of the perception of colors by the subject at two respective separate times $t_1$ and $t_2$. Preferably, the teachings of the invention and in particular the method described above with reference to FIGS. 1 to 4 are used.

The two indicators or biomarkers are obtained, in steps 50 and 51, using the same dynamic multi-color, typically two-color, stimulus: same fixed color $C_1$, same modification profile 410 of the color $C_2$, same tagging frequency $F_{tag}$, etc.

The two indicators or biomarkers are of same nature and are for example two signals $SIG_{power}(t_1)$ and $SIG_{power}(t_2)$ 460, two approximation signals $APPROX_{power}(t_1)$ and $APPROX_{power}(t_2)$, or two iso-luminance configurations 499 (or more simply the two non-zero values $c_2(t_1)$ and $c_2(t_2)$ of $C_2$ corresponding to the chromatic iso-luminance of the two tests carried out).

These two indicators or biomarkers are then compared in step 52 in order to determine an indicator 53 representative of a modification between the two signals representative of the oscillation power of the pupil.

For example, the modification indicator 53 is the difference between the average values of these two signals:

average[$SIG_{power}(t_1)$]−average[$SIG_{power}(t_2)$], or average[$APPROX_{power}(t_1)$]−average[$APPROX_{power}(t_2)$]

As a variant, the modification indicator 53 is the difference between the color values of the two chromatic iso-luminance configurations: $c_2(t_1)−c_2(t_2)$.

It is this modification indicator 53 that forms an effective indicator or biomarker characteristic of a potential pathology of the subject.

The modification indicator 53 may then be used to diagnose a pathology or to track the progress of a pathology of the subject.

For example, in step 54, the modification indicator 53 is compared to a threshold value 55. If the modification indicator 53 exceeds this threshold value, then a pathology is diagnosed or a degradation in the pathology is concluded (step 56).

Specifically, the inventors have observed that a degradation of the eye (of the chromatic photoreceptors), of optical pathways (the optical nerve) or of visual cerebral areas leads to a decrease, which is sometimes significant, in the oscillatory power of the pupil and/or to a significant modification in the perception of colors.

Thus, by way of example, the modification indicator 35 may be used to track a potential intoxication of a patient operated for a hepatitis by short-circuit of the liver. In particular, if the chromatic green iso-luminance value with pure red (140, 0, 0) drops by more than 40 units with respect to the value measured before operation, then a suspicion of intoxication is diagnosed.

The inventors have in particular observed that this indicator or biomarker 53 is an effective way of detecting progressive phases of multiple sclerosis (MS) or of tracking this progression in case of (sometimes experimental) medical treatment. The current techniques used for this detection are in particular based on visually evoked potentials (VEPs) that are sensitive to artefacts due to movement of the subject, and that require long measurement sessions and complex equipment (electrodes). The use of the indicator or biomarker 53 according to the present invention avoids these constraints.

The inventors have also observed that this indicator or biomarker 53 is suitable for tracking the neurological progression of certain pathologies or resulting from interventions due to these pathologies, examples being diabetes and hepatitis (because of post-operative intoxications). It therefore also makes it possible to detect any pathology that degrades the perception of colors (by degrading the neurological system of the subject), such as neurodegenerative diseases (Alzheimer's, Parkinson's), neurodevelopmental diseases (schizophrenia, autism), neurovascular diseases (stroke), intoxications (affecting the neurological system), age-related macular degeneration, glaucoma and retinal diseases, etc.

Specifically, the degradation of neurological zones (optical nerves, visual cerebral areas) leads to a sometimes significant modification in the perception of colors by the subject. In contrast, a healthy subject preserves a perception of colors that is relatively constant over time (even if it does change slightly with age).

The publication "Colour vision deficiencies in Alzheimer's disease" (Patche M. et al., 2003) has for example demonstrated a deterioration in the color vision of subjects afflicted with Alzheimer's disease. The publication "Abnormalities in color vision and contrast sensitivity in Parkinson's disease" (Price M. J. et al., 1992) has done the same for Parkinson's disease. The publication "Reversible color vision defects in obstructive jaundice" (Varnek L. et al., 1981) also makes the link between a degradation of the perception of colors and intoxications related to liver treatments. The publication "Diabetic retinopathy seeing beyond glucose-induced microvascular disease" (Antonetti D. A. et al., 2006) makes the link between diabetes and degradation of the retina, and therefore of the perception of colors.

Certain pathologies (for example neurological diseases) affect both eyes of the studied subject. Thus, one indicator/biomarker 53 may be generated for each of the two eyes. In this case, it is determined whether each indicator is significantly degraded. As a variant, an average of the two markers may be used.

Other pathologies have more localized effects, generally affecting a single eye. This is in particular the case of ophthalmological diseases (glaucoma, retinal disease), but also the case of certain neurological diseases (for example multiple sclerosis may affect a single optical nerve and cause a local optical neuritis). Such pathologies may be detected when a single of the two generated indicators/biomarkers 53 is significantly degraded. Reciprocally, these indicators 53 allow the zone (i.e. the eye) affected by a disease to be located (for example in the aforementioned case of multiple sclerosis).

The preceding examples are merely embodiments of the invention, which is not limited thereto.

The invention claimed is:

1. Method for generating an indicator or biomarker ($SIG_{power}$, $APPROX_{power}$) of the perception of colors by a mammal subject, comprising the following steps:
    subjecting the mammal subject to at least one dynamic multi-color stimulus comprising displaying, on a display peripheral, a multi-color pattern at least two colors of which are periodically inverted at a frequency called the tagging frequency ($F_{tag}$),
    controlling a modification over time of at least one ($C_2$) of the two colors of the multi-color pattern during the display of the dynamic multi-color stimulus, in order to make the displayed luminance of this color vary,
    acquiring, with an image-acquiring device, an oscillatory response ($SIG_{resp}$) of at least one pupil of the mammal subject, during the display of the dynamic multi-color stimulus, and
    generating, from the acquired response, a signal ($SIG_{power}$, $APPROX_{power}$) representative of the power of the oscillatory response ($SIG_{resp}$) of power, the pupil as a function of the modification over time of at least one of the two colors during the display of the dynamic multi-color stimulus.

2. The method according to claim 1, further comprising a step of determining the iso-luminance two-color configuration of the two colors of the dynamic multi-color stimulus corresponding to a minimum (MIN) of the generated signal ($SIG_{power}$, $APPROX_{power}$).

3. The method according to claim 1, wherein the other color ($C_1$) of the multi-color pattern is kept fixed during the display of the dynamic multi-color stimulus.

4. The method according to claim 1, wherein the tagging frequency ($F_{tag}$) is dependent on the subject.

5. The method according to claim 4, further comprising a prior step of determining the tagging frequency ($F_{tag}$), by subjecting the subject to at least one calibration light flash, measuring an average response time of the pupil of the mammal subject to the calibration light flash, and setting the tagging frequency depending on the measured average response time.

6. The method according to claim 1, wherein the mammal subject is subjected to two successive dynamic multi-color stimuli based on two different pairs of colors.

7. The method of claim 6, wherein multi-color stimuli are two-color stimuli.

8. The method according to claim 1, wherein the generated signal is a signal representative of the oscillation power of the pupil at the tagging frequency and/or at one or more of its harmonics, representative of the variation in the frequency component, at said tagging frequency and/or at one or more of its harmonics, of the oscillatory response of the pupil.

9. The method according to claim 8, wherein the generation of the signal representative of the oscillation power ($SIG_{power}$, $APPROX_{power}$) of the pupil at the tagging frequency ($F_{tag}$) and/or at one or more of its harmonics comprises applying, to the acquired response ($SIG_{resp}$), a discrete fast Fourier transform in a moving time window ($W_i$) and storing in memory, for each time window, the value ($P_{i,tag}$) of the frequency component at the tagging frequency and/or at one or more of its harmonics of the obtained frequency spectrum.

10. The method according to claim 1, wherein the generation of the signal representative of the power of the oscillatory response comprises determining an amplitude of variation in the diameter of the pupil in response to each inversion of the colors of the multi-color pattern, said signal ($SIG_{power}$, $APPROX_{power}$) being formed from the amplitudes thus determined.

11. Method for determining an indicator or biomarker characteristic of a pathology of a mammal subject, comprising the following steps:
    generating at least two indicators or biomarkers ($SIG_{power}$, $APPROX_{power}$) of f the perception of colors by the mammal subject at two separate respective times ($t_1$, $t_2$), by performing the method according to claim 1, and
    determining an indicator characteristic of a pathology by the modification between the two separate respective times thus generated power signals ($SIG_{power}$, $APPROX_{power}$) of the pupil.

12. The method according to claim 11, wherein the step of generating at least two indicators or biomarkers comprises determining, for each of the two times ($t_1$, $t_2$), the iso-luminance two-color configuration of the two colors of the dynamic multi-color stimulus corresponding to a minimum (MIN) of the generated signal ($SIG_{power}$, $APPROX_{power}$), and the modification indicator comprises a difference between the color values ($c_2(t_1)$, $c_2(t_2)$) of the two determined two-color configurations.

13. Method to diagnose a pathology or to track the progress of a pathology of a mammal subject, comprising a step of providing a modification indicator obtained for the mammal subject by performing the method according to claim 11, and diagnosing the pathology or tracking the progress of the pathology based on the modification indicator.

14. The method according to claim 13, wherein the pathology is selected from the group consisting of: multiple sclerosis, hepatitis, diabetes, neurodegenerative diseases, neurodevelopmental diseases, neurovascular diseases, intoxications, age-related macular degeneration, glaucoma and retinal diseases.

15. The method according to claim 14, wherein the neurodegenerative disease is selected from the group consisting of: Alzheimer's and Parkinson's disease.

16. The method according to claim 14, wherein the neurodevelopmental disease is selected from the group consisting of: schizophrenia and autism.

17. The method according to claim 14, wherein the neurovascular disease is stroke.

18. The method of claim 1, wherein the multi-color stimulus is a two-color stimulus and the multi-color pattern is a two-color pattern.

19. System for generating an indicator or biomarker ($SIG_{power}$, $APPROX_{power}$) of the perception of colors by a mammal subject, comprising:
  a display peripheral,
  a computational system for stimulating the mammal subject with a dynamic multi-color, stimulus, the computational system controlling the display, on the display periphery, of a multi-color pattern at least two colors of which are periodically inverted at a frequency called the tagging frequency ($F_{tag}$),
  a color controller configured to modify over time at least one ($C_2$) of the two colors of the multi-color pattern during the display of the dynamic multi-color stimulus, in order to make the displayed luminance of this color vary,
  an image-acquiring device for acquiring an oscillatory response ($SIG_{resp}$) of at least one pupil of the mammal subject, during the display of the dynamic multi-color stimulus, and
  an indicator or biomarker generator configured to generate, from the acquired response, a signal ($SIG_{power}$, $APPROX_{power}$) representative of the power of the oscillatory response ($SIG_{resp}$) of the pupil as a function of the modification over time of at least one of the two colors during the display of the dynamic multi-color stimulus.

20. System for determining an indicator or biomarker characteristic of a pathology of a mammal subject, comprising:
  a system for generating an indicator or biomarker of the perception of colors by a mammal subject according to claim 19, and
  a processing module configured to determine an indicator of modification between two power signals ($SIG_{power}$, $APPROX_{power}$) generated, by the system for generating an indicator or biomarker of the perception of colors, at two separate times ($t_1$, $t_2$) for the same subject using the same dynamic multi-color stimulus.

21. The method according to claim 19, wherein the multi-color stimulus is a two color stimulus.

22. The method according to claim 19, wherein the multi-color pattern is a two color pattern.

* * * * *